United States Patent
May, III

[19]

[11] Patent Number: 6,019,227
[45] Date of Patent: Feb. 1, 2000

[54] EXTRACTOR AND SEPARATOR APPARATUS

[76] Inventor: Alexander Douglas May, III, P.O. Box 818, Chipley, Fla. 32428

[21] Appl. No.: 08/895,670

[22] Filed: Jul. 17, 1997

Related U.S. Application Data

[63] Continuation of application No. 08/340,244, Nov. 16, 1994, abandoned.

[51] Int. Cl.$^7$ ............................................. B07B 1/18
[52] U.S. Cl. ........................... 209/284; 209/288; 209/291; 209/421
[58] Field of Search ............................. 209/284, 285, 209/286, 288, 289, 290, 291, 420, 421

[56] References Cited

U.S. PATENT DOCUMENTS

| | | | |
|---|---|---|---|
| 3,942,644 | 3/1976 | Vissers | 209/284 X |
| 4,114,762 | 9/1978 | Beal et al. | 209/615 |
| 4,147,256 | 4/1979 | Kiss | 209/632 |
| 4,156,508 | 5/1979 | Kisielewski | 209/284 X |
| 4,915,826 | 4/1990 | Nordhus | 209/288 |
| 5,019,248 | 5/1991 | Kaldor | 209/291 X |

FOREIGN PATENT DOCUMENTS

| | | | |
|---|---|---|---|
| 1546177 | 2/1990 | U.S.S.R. | 209/288 |

*Primary Examiner*—Tuan N. Nguyen

[57] ABSTRACT

The present invention is an apparatus that will extract a desired material from an undesired material. The apparatus of the present invention comparison a front portion, a middle portion, and a back portion. The front portion includes the driving method for the device as well as a plurality of teeth which contacts the undesired material containing the desired material and transports the collection to the middle area via a conveyor. The middle portion includes the separating area. The middle portion includes a rotating cylinder including a series of sections. At least one encompassing side wall of a section is made of a wire mesh material to provide for the section to have a plurality of perforations. This will provide for the undesired material to escape from the middle portion via the openings of the wire mesh. From the middle portion, the collected material travels to the back portion where the desired material is collected in a receptacle.

19 Claims, 3 Drawing Sheets

EXTRACTOR AND SEPARATOR APPARATUS

This is a File Wrapper Continuation of Application Ser. No. 08/340,244, filed on Nov. 16, 1994, abn.

BACKGROUND OF THE INVENTION

1. Field of the Invention

The present invention relates to an apparatus that is used to extract and separate a desirable material from an undesirable material, and more particularly the present invention relates to a self propelled apparatus that will quickly and efficiently extract items, such as worms, and separate the items from the undesirable item, such as soil.

2. Description of the Background Art

Through out the United States, efforts are being taken to improve the efficiency of collecting and separation a desirable material from an undesirable material. The primary cost component of collecting and separating a material from an undesirable material (i.e. collecting and separating worms from the soil) is labor. In the past, the collection and separation of such material has been done manually. Individuals must contact and extract the desired material from the undesirable material. Though efficient, the process has been very time consuming. Accordingly, many efforts have been devoted to reduce the labor cost component of preparing the extraction and separation of the desired material from the undesired material. With the advent of cost and time containment throughout the various industry, renewed efforts are being made to examine all direct labor cost areas with a focus on reducing the amount of labor heretofore involved, and the associated cost.

For example, U.S. Pat. No. 4,147,256, issued to Kiss discloses a stationary separating apparatus that includes a feed hopper and a screen means. Worms and their habitat (i.e. earth, eggs, peat moss) are dropped through the hopper to fall to the screen means. The screen means consists of a feed section, an intermediate section, and a downstream section. The feed section is at a higher elevation and the downstream is at a lower elevation. As the worms and their habitat travel across the screen means, the earth, eggs, peat moss, and smaller sized worms are filtered out via the screen means to provide for the desired worms to be transported to a holding receptacle. The problem with Kiss's apparatus is that it is not self propelled. A second problem is that an individual still must dig the worms and their habitat first and then lift the collection to drop it into the hopper, accordingly not reducing the labor cost associated with collecting the undesired material containing the desired material.

U.S. Pat. No. 4,114,762 issued to Beal et al. disclose a separating apparatus. This separating apparatus consists of a rotatable hollow, cylindrical drum having a delivery chute disposed at its inlet opening. The drum is mounted for rotation about an axis which is disposed at a slight angle or incline to the true horizontal. The interior surface of the drum is provided with a plurality of extending worm gathering projections. The worms and their habitat are dropped in the inlet opening and travel through the drum. During the traveling process, the worms are collect and maintained via the worm gathering projection while the undesired material exists the drum. This apparatus does not decrease labor since an individual still must collect the habitat with the worms and drop the collection into the inlet. Additionally, after the separation has occurred, an individual must still remove the worms located between the projections and place the worms in a receptacle.

None of these previous efforts, however, provide the benefits intended with the present invention. Additionally, prior techniques do not suggest the present inventive combination of component elements as disclosed and claimed herein. The present invention achieves its intended purposes, objectives and advantages over the prior art device through a new, useful and unobvious combination of component elements, which is simple to use, with the utilization of a minimum number of functioning parts, at a reasonable cost to manufacture, assemble, test and by employing only readily available material.

SUMMARY OF THE INVENTION

The present invention relates to a self propelled apparatus which will extract a desired item from the undesirable item (i.e. worms, peanuts, rocks, potatoes, etc. from soil or oil from sand).

The apparatus of the present invention comprises a front portion, a middle portion, and a back portion. The front portion includes the driving mean of the apparatus. The middle portion constitutes the separating area, and the back portion includes the means for holding and maintaining the desirable material.

The desirable material is extracted from the desirable material via a plurality of elongated flat teeth which are located in the front portion of the apparatus. These teeth extend into the desirable material (i.e. soil or sand) for the purpose of loosening the material and enabling the desired material to be removed. The desirable material and some of the undesirable material are transported to the separating area via a conveyor belt. It is in this area that the first stage of the separating process occurs. This area includes a single cylinder or a plurality of cylinders. These cylinders rotate to aid and expedite the separating process. The cylinder(s) includes a mesh or wire-like material that varies in wire mesh size from the start of the separating area to the end of the separating area. For example, if worms are the desired product and the soil is the undesirable product, then the worms and soil will enter the separating area. At the first station, the size of the wire mesh is sufficiently small enough to enable the soil to escape from the cylinder(s) and return to the ground while the worms remain in the cylinder. At the next station, the wire mesh will be decreased or increased in sized to permit for more soil, as well as smaller sized worms to be separated from the larger size worms. These smaller sized worms exit the separating area via the wire mesh of the mesh materials and are returned to the soil. This mesh eventually increases or decreases in size so that the desired product can remain in the cylinder while the undesirable material exits the cylinder via the mesh materials.

From the separating area, the desired items are directed to a holding receptacle. Some undesirable material may still remain in the cylinder. Since the desirable material is different from the undesirable material, it will inherently posse different densities, texture, and physical characteristics, and as such will inherently travel at different velocities. This will enable for the desired material to be directed to a holding receptacle while the undesired material is returned to its environment.

Accordingly it is the object of the present invention to provide for an apparatus that will effectively and efficiently extract a desired material from an undesirable material as well as successfully separate the desired material from the undesired material.

It is another object of the present invention to provide for an apparatus that will extract a desirable material from an undesirable material and separate the desired material from the undesired material using minimal or no manual labor.

It is a further object of the present invention to provide for an apparatus that will substantially increase the production of removing and separating the desired material from the undesirable material.

A final object of the present invention, to be specifically enumerated herein, is to provide an extracting and separating apparatus in accordance with the preceding objects and which will conform to conventional forms of manufacture, be of simple construction and easy to use so as to provide a device that would be economically feasible, long lasting and relatively trouble free in operation.

Although there have been many inventions related to a worm extracting device none of the inventions have become sufficiently compact, low cost and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, other objects and a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

Similar reference numerals refer to similar parts throughout the several views of the drawings.

DESCRIPTION OF THE PREFERRED EMBODIMENTS

Figure 1:
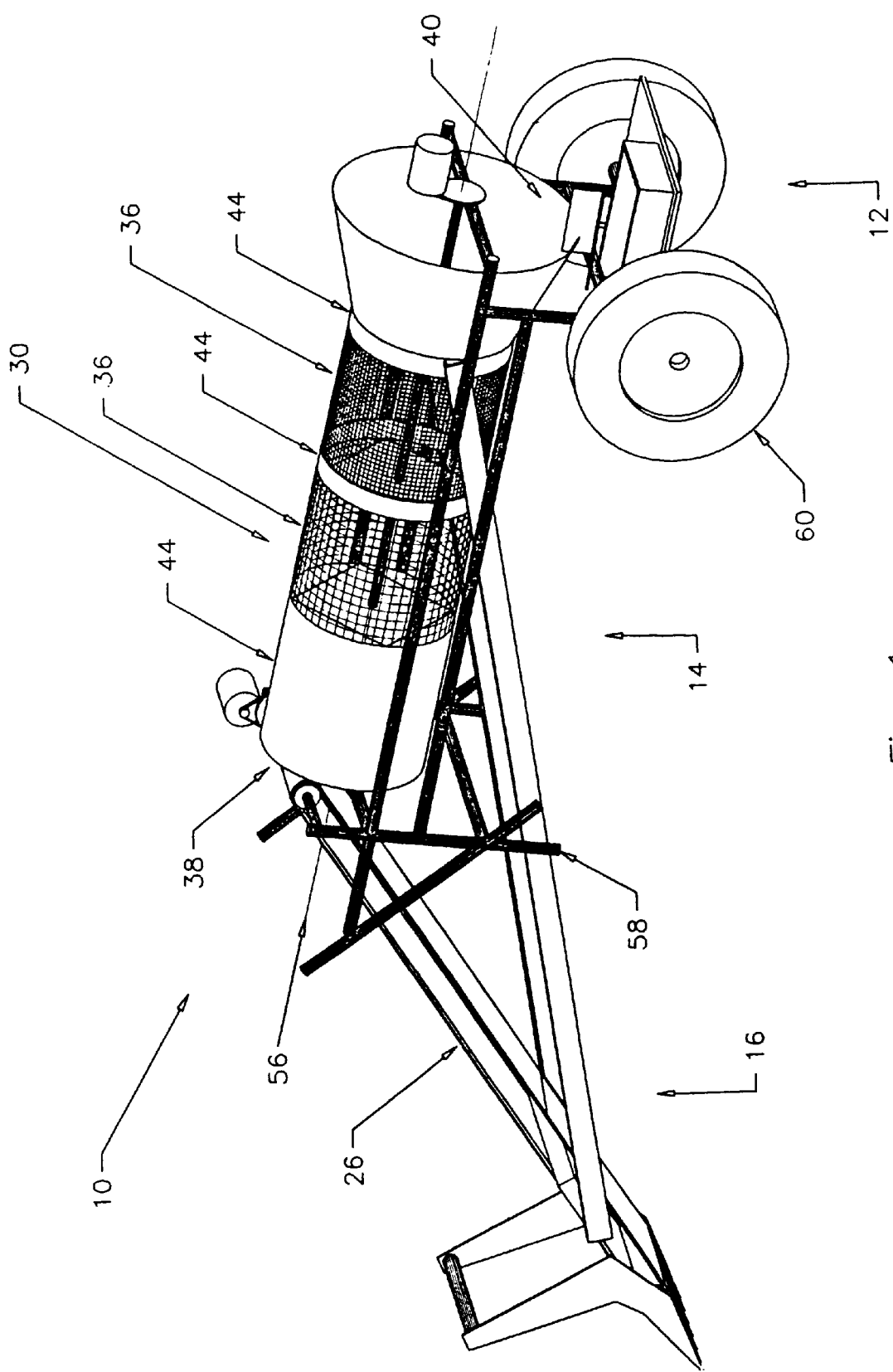
FIG. 1 is a perspective side view of the apparatus of the present invention.

As illustrated in the drawings, the extracting and separating apparatus 10 of the present invention is comprised of a back portion 12, a middle portion 14, and a front portion 16. The back, middle and front portions are maintained on a frame 58 (partially illustrated).

The back portion 12 includes a pair of wheels 60 while the front portion is attached to the driving means (not illustrated). This driving means can be permanently attached to the front portion 16 of the apparatus or the apparatus itself can be adapted to be removable secured to a conventional driving means (i.e. tractor). The combination of the driving means and wheels will permit for the device to travel while simultaneously extracting and separating the desired material from the undesired material (i.e. worms from the earth or soil).

Figure 2:
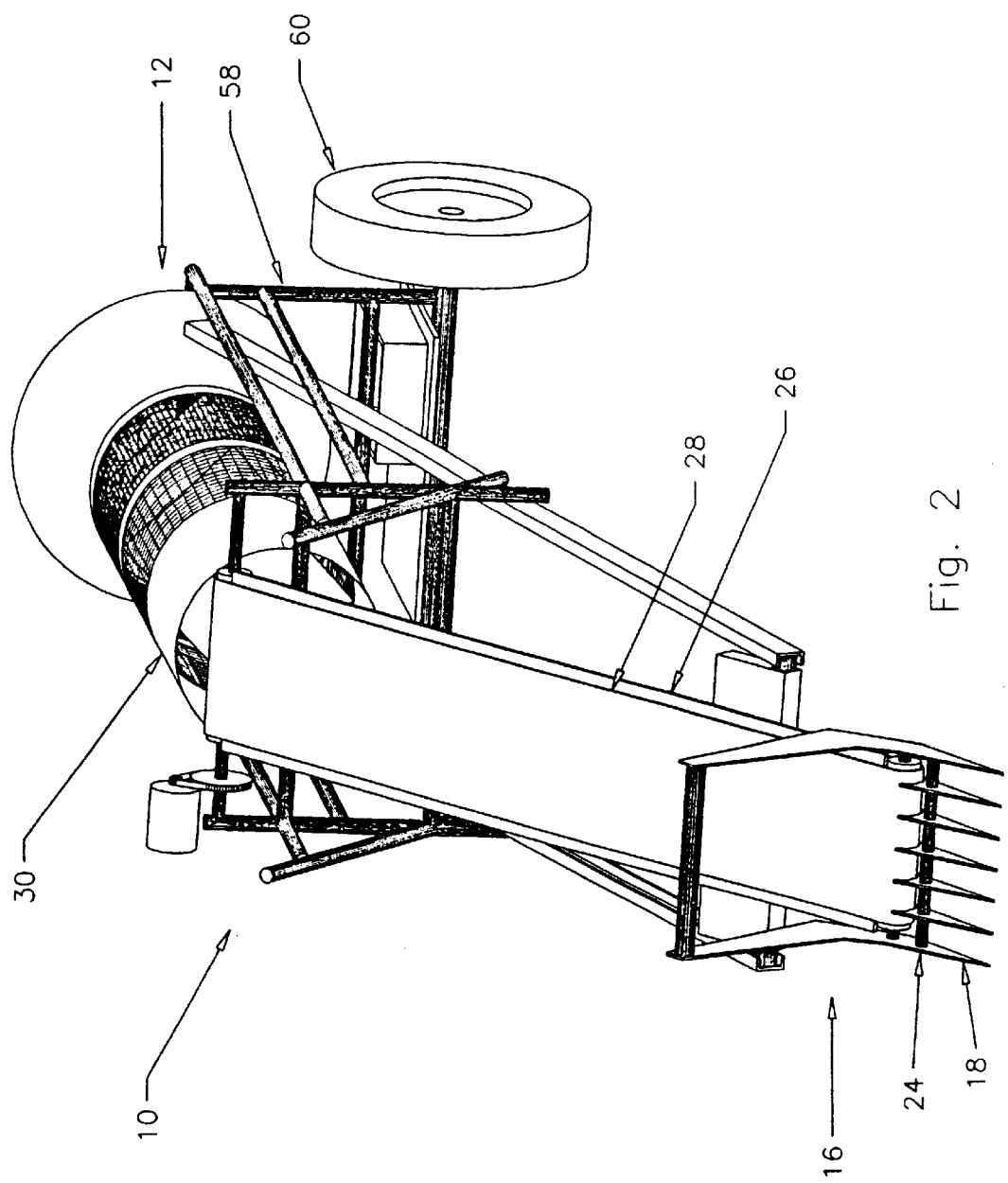
FIG. 2 is a perspective front view of the apparatus of the present invention.

The front portion 16 constitutes the extracting area. This front portion 16 is illustrated in further detail in FIG. 2. As seen in this figure, the extracting area consists of a plurality of parallel, evenly spaced apart teeth 18 that are normal to the undesirable material. These teeth 18 are in the shape of a wedge and each one includes a sharp point. The sharp point faces away from the front portion 16 of the apparatus 10 and is in direct communication with the undesirable material. The teeth are maintained on the front portion via a shaft 24 to permit for the plurality of teeth to be attached to the front portion of the apparatus 10 of the present invention. Accordingly, as the driving means (power unit or tractor-like device) propels the apparatus forward (teeth travel towards the power unit or tractor-like device), the points of the teeth 18 will be dragged through the undesirable material (i.e. soil or sand). This arrangement will allow the teeth to loosen the undesirable material (i.e. soil) and render the undesirable material containing the desirable material to travel up the incline of the teeth 18 and onto a conveyor 26. A depth altering means can permit a user to alter the depth of which the teeth contact the dirt. This depth altering means can be any conventional means to alter the teeth 18. For example the teeth can be adjusted by a hydraulic lift (not illustrated) on the driving means (i.e. power unit or tractor-like device) similar to a conventional plow. This will provide for the shaft located above the teeth (illustrated, but not labeled) to be pulled forward, inherently providing for the point of the teeth to move towards the ground.

The conveyor 26 enables the undesirable material (i.e. soils) containing the desired material (i.e. worms) to be directed to the middle portion 14 or separating area. The conveyor acts as a transport apparatus for permitting the material to be transported from the front portion to the middle portion. This conveyor 26 extends into an opened inlet 38 of a cylinder 30.

The conveyor belt is of a conventional type and includes a first pulley and a second pulley (both partially illustrated, but not labeled). These pulleys are controlled by and powered by a first motor (illustrated, but not labeled). This first motor would be attached to the frame (this configuration is not shown). The first pulley is located in the proximity of the plurality of teeth 18 and the second pulley is located in the proximity of the separating area or middle portion 14. Encompassing the first and second pulley is a substantially flat material 28. The undesired and desired material travel on the substantially flat material 28 of the conveyor 26 to the middle portion 14.

The conveyor 26 connects the front portion 16 to the middle portion 14 of the apparatus 10. This connection occurs at an acute angle with respect to the teeth 18 of the front portion 16. This conveyor 26 extends into the opened inlet 38 of the cylinder 30. Due to the combination of the upward angle and that the conveyor 26 extends into the opened inlet 38 of the cylinder 30, the desired material and undesired material are able to drop and fall freely (i.e. gravity) into the middle portion 14.

Figure 3:
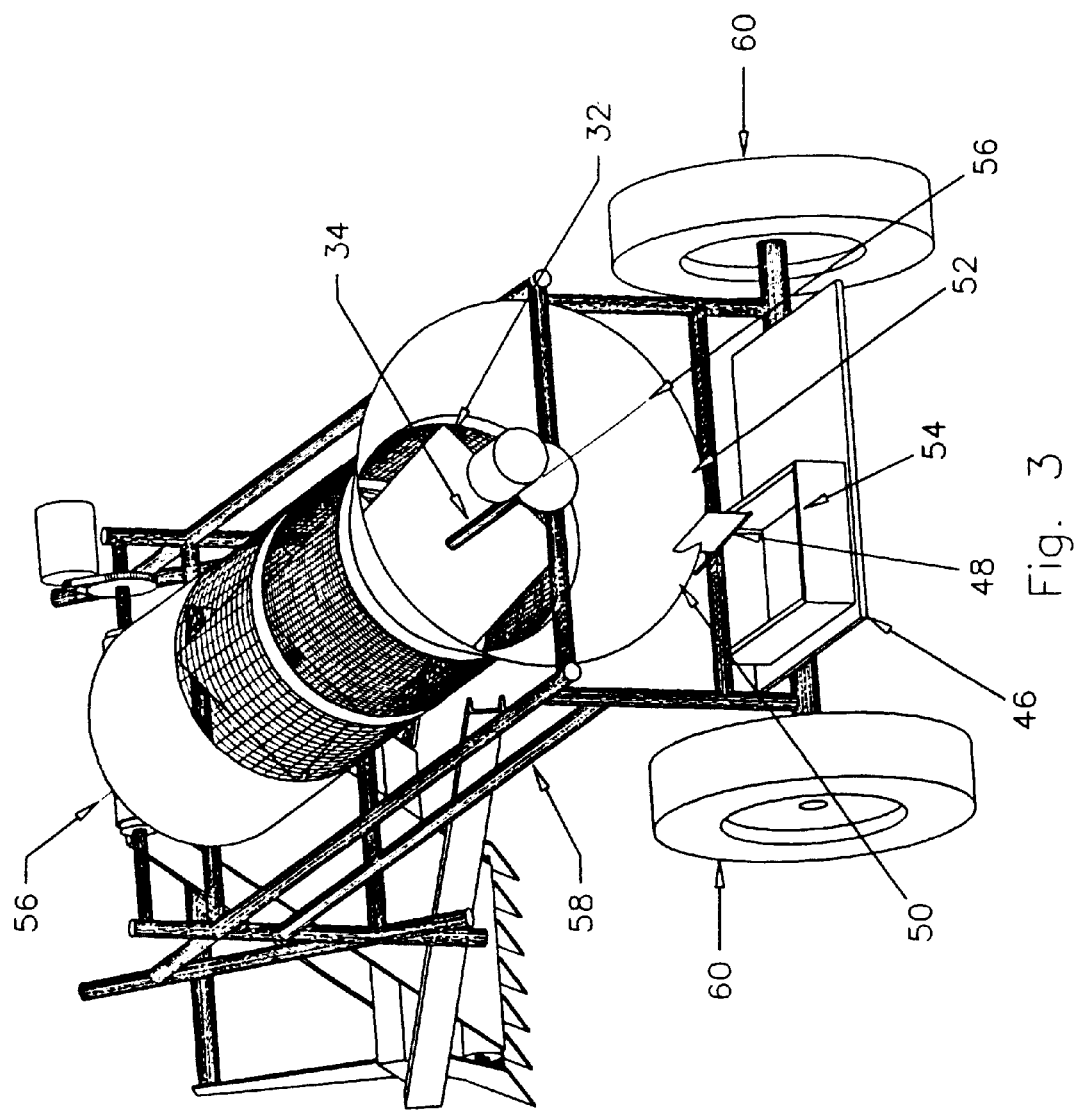
FIG. 3 is a perspective back view of apparatus of the present invention.

The middle portion 14, which constitutes the separating area, includes two embodiments. The first embodiment is illustrated in further detail in FIGS. 1–3. As seen in these figures, the middle portion 14 consists of an elongated, and hollow cylinder 30 having an opened inlet 38 that receives the collection (desirable material and undesirable material) and an opened outlet 40. The cylinder is also mounted for rotation about an axis 56. As illustrated in the figures, the cylinder is disposed at an obtuse angle or incline to provide for the cylinder 30 to be in a downward direction from the opened inlet 38 to the opened outlet 40.

The rotation of the cylinder is accomplished by interiorly attaching at least one plate or cross-bar 32 (illustrated in this figure as a plate) to the encompassing wall of the cylinder. Centrally attached to the plate(s) 32 or cross-bar is a rod 34. This rod is attached to the shaft of a motor (this motor is illustrated, but not labeled). Accordingly, this design will permit for the rod to rotate, which in turn will cause the rotation of the plate(s) or cross bar 32 inherently causing the rotation of the cylinder 30. The encompassing side wall of the rotating cylinder is fabricated from a plurality of different material having different densities or made of different types of wire meshes. These different materials provide for the elongated cylinder to have a plurality of sections 36.

These sections 36 aid in the separation and removal of unwanted material from the desired material. The conveyor 26 drops the collection of material (undesired and desired) into the opened inlet 38 of the cylinder 30. The combination of the rotation of the cylinder and the attachment at an incline provide for the material to inherently travel forward.

While traveling within the cylinder, the collected material will come into contact with a first section. This first section, as illustrated is a solid wall. The collect material will come into contact with the solid wall and upon impact will provide for the desired material to separate from the undesired material. Additionally, the contact with the solid wall will provide for the undesired material to break into smaller pieces. The material will travel forward and will contact a second section. This second section consists of a first wire mesh having a predetermined grid (rectangular perforations therein). As the cylinder is rotating, the material within the cylinder rotates and moves about the cylinder. During the rotational movement, the collection of material will contact the inner surface of the encompassing side wall. This contact provides for a force to be exerted onto the collection. This arrangement and configuration will permit for the undesired material to extract itself from the desired material. Additionally, the undesired material that is smaller in diameter than the diameter of the perforations of the wire mesh is able to escape from the second section (via the rectangular perforations) and return to its original environment. The desired material and some pieces of undesired material will remain trapped in the cylinder. For example, if soil containing worms is transported to the separating area via the conveyor, the dirt clogs that are collected will contact the solid encompassing side wall. This contact will provide for the dirt clogs to break into smaller pieces. The loose dirt can then escape by way of the openings within the wire mesh of the second section. The worms will remain trapped within the cylinder. The remaining material will continually be in contact with the side walls of the cylinder. Inherently breaking down into smaller and smaller pieces.

The rotation of the cylinder is continued and the collection is directed forward. After the encounter with the first wire mesh, the collection experience another encounter with a second wire mesh. This figure illustrates a second wire mesh includes perforations which are smaller than the perforations of the first wire mesh. However, it is noted that the perforations of the first wire mesh can be smaller than the perforations of the second wire mesh.

The first wire mesh illustrated in these figures will permit for larger, undesired material to exit the cylinder. In the example above, the same scenario would permit the smaller, undesired worms to escape and return to the soil via the perforations within the first and second meshes. Additionally, larger pieces of soil can also be removed from the cylinder via the larger openings within the wire mesh. The collection travels forward to permit for additional pieces to be shifted out via the perforations of the second wire mesh.

The undesirable material and the desirable material continue to travel along the rotating cylinder. The number of sections and the size of the openings within the mesh is dependent on the items which are to be extracted and separated from the undesirable material.

The undesirable material that is remaining and the desired material continue along the cylinder 30, until contact is made with an encompassing wall that is solid 44.

At this point the remaining material exists the middle portion via the outlet 40 and enter the back portion 12. This back portion 12 is illustrated in further detail in FIG. 3.

The middle portion 14 can also include a second embodiment. This second embodiment is not separately illustrated. In this embodiment the middle portion is fabricated from a plurality of hollow cylinders. These cylinders are in direct alignment with one another. The first cylinder includes the opened inlet while the last cylinder includes the opened outlet. Each cylinder includes a first end and a second end. Each second end of the preceding cylinder is located as closely as possible and without contacting the first end of the succeeding cylinder.

Each cylinder includes an encompassing side wall wherein at least one includes a grid (perforations therein). Each cylinder is attached to a motor in the same manner as the cylinder of the first embodiment, in order to permit for the rotation of each cylinder. A second motor, one that is reverse drive, can be used in order to provide an alteration in the direction of rotation of the plurality of cylinders. For example, if three cylinders where used, then the first and third cylinder can be in direct communication with the first motor to permit for the rotation of the cylinders to occur in one direction, while the middle cylinder is in direct communication with the second motor to provide for the middle cylinder to rotate in a opposite direction than the first and third cylinders.

The cylinders in this second embodiment will operate and function in the same manner as with the first embodiment of the middle portion as discussed and illustrated in the figures. Accordingly, the collection (desirable material and undesirable material) will enter the middle portion via the opened inlet of the first cylinder. The smaller sized pieces of undesired material are able to escaped via the perforations of the mesh material of the first cylinder. From there the remaining material travels to the succeeding cylinders until the collection reaches the back portion.

From the middle portion, the remaining material (desirable and undesirable) travels to the back portion 12. The back portion is illustrated in further detail in FIG. 3. As illustrated, the back portion 12 includes a platform 46 which extends with a slight angle downwardly from the middle portion. Extending outwardly and perpendicularly from the platform is a dividing plate 48. The dividing plate separates the first side 50 of the platform 46 from the second side 52 of the platform. Located on the platform and on the first side 50 is a receptacle 54. This receptacle 54 receives the desired material.

Since the desirable material is different from the undesirable material, it will inherently posses different densities, texture, and physical characteristics, and as such will inherently travel at different flow rate and velocities. This will enable for the desired material to be directed to first side of the platform to a holding receptacle while the undesired material is returned to its environment via the second side.

For example, in the case of collecting worm, the remaining dirt, dirt clogs, and worms are able to travel towards the back portion 12 of the apparatus 10. Here the worms come into contact with an encompassing wall that is solid. The worms and remaining dirt rotate about the last section of the elongated cylinder 10. Due to the weight and density of the worms in comparison to the dirt, the worms are shifted to a first side 50 of the platform 46 while the remaining dirt is travel directly downward to the second side 52 of the platform. Located at the first side 50 of the dividing plate is a receptacle 54 which catches and maintains the desired worms.

As stated previously, this apparatus can also be utilized in different environments to produce the same results. The example given throughout the specification has been one of separating worms from the earth, however this apparatus can also be used within the sand. For example, this apparatus can also be used to extract oil from sand. In this example, the teeth would collect the sand and oil onto the conveyor. From the conveyor, the sand and oil would travel to the separating area wherein the separation of the clean sand from the oil drench sand would occur.

This invention is not limited to solid material but can also be design for use in water. For example, the driving means can be a boat and the wheels on the front end can be replaced with floatation devices. This arrangement will permit for safely gathering shrimp or oysters (desired material) and separating this desired material from undesired material (water, sand, shells, vegetation, etc.).

Additionally, the frame can be increased in width to enable the use the of a plurality of cylinders with independent back portions. The plurality of cylinders will be aligned in a parallel relation. In this design, the amount of teeth would increase as well as the width of the conveyor. This arrangement will increase the surface area covered for the extraction of undesired and desired material to inherently increase the amount of desired material collected. Accordingly, the front teeth would enable the desired material containing the undesired material to travel up the enlarged and widen conveyor. The collection would be dropped into the openings of the plurality of parallel aligned cylinders.

While the invention has been particularly shown and described with reference to an embodiment thereof, it will be understood by those skilled in the art that various changes in form and detail may be made without departing from the spirit and scope of the invention.

I claim:

1. An extracting and separating apparatus to be used for collecting and separating a desired material from an undesired material comprising:
    a front portion, a middle portion, and a back portion;
        said front portion is attached to a driving means for propelling said separating apparatus on a surface which contains said undesired material having said desired material, and for activating said separating apparatus;
        said front portion includes an extraction mechanism for collecting said undesired material containing said desired material, and said extraction means collects said undesired material having said desired material while propelling across said surface for enabling collecting and separating to occur simultaneously;
    a transport apparatus located between said front portion and said middle portion, said transport apparatus being adapted for receiving said undesired material containing said desired material from said extraction unit and to transport said undesired material containing said desired material to said middle portion;
    said middle portion includes a cylinder which is mounted for rotation about a substantially horizontal axis and having a first section having an inlet end with a first encompassing wall and a downward section having an outlet end with a second encompassing wall to provide for said outlet end to be an opened end of said second encompassing wall, and at least an area of said cylinder is perforated for progressively and selectively filtering said desired material from said undesired material from said inlet end to said outlet end and said outlet end extends into said back portion, and said inlet end is located opposite from said outlet end and at a true horizontal;
    a receptacle for receiving said desired material is located in said back portion; and
        said second encompassing wall flares outwardly for providing said outlet end to be larger in size than said inlet end.

2. An apparatus as in claim 1 wherein said transport apparatus comprising a conveyor and said conveyor includes a first end and a second end, said extraction unit is located in proximity to said first end and said second end is located in proximity to said middle portion, said conveyor is disposed at a slight angle to the true horizontal in an upward direction from said first end to said second end.

3. An apparatus as in claim 2 wherein said extraction unit includes a plurality of parallel, evenly spaced teeth that are normal to said undesirable material.

4. An apparatus as in claim 1 wherein said axis of rotation of said cylinder is disposed at a slight angle to the true horizontal in a downward direction from said opened inlet to said opened outlet.

5. An apparatus as in claim 3 wherein said extraction unit includes a depth altering device for alternating a deepness that said plurality of teeth will pierce said undesirable material.

6. An apparatus as in claim 1 wherein said middle portion further includes said area to be a first middle section located between said first section and said downward section, and said first middle section having a third encompassing wall and said third wall is perforated.

7. An apparatus as in claim 6 wherein said middle portion further includes a second middle section located between said first section and said first middle section, said second middle section having a fourth encompassing wall and said fourth encompassing wall is perforated, and said first encompassing wall and said second encompassing wall are solid.

8. An apparatus as in claim 7 wherein said third encompassing wall includes holes of a first size and said fourth encompassing wall includes holes of a second size providing said first size are different measurement than said second size.

9. An apparatus as in claim 8 wherein said first size is larger than said second size.

10. An apparatus as in claim 8 wherein said first size is smaller than said second size.

11. An apparatus as in claim 1 wherein said back portion includes a platform that is located in the proximity of said opened outlet and is disposed at a slight angle to the true horizontal in a downward direction from said opened outlet, said platform includes a first side, as second side, a first end and a second end, said first end is located in the proximity of said opened outlet, a dividing plate extends perpendicularly and outwardly from said platform and divides said first side from said second side, and said receptacle is located on said second side for permitting said desired material to flow on said first side and fall into said receptacle and for larger portions of said undesirable material to flow off said apparatus via said second side.

12. An extracting and separating apparatus to be used for collecting and separating a desired material from an undesired material comprising:

a front portion, a middle portion, and a back portion;

said front portion is attached to a driving means for propelling said separating apparatus on a surface which contains said undesired material having said desired material, and for activating said separating apparatus;

said front portion includes an extraction mechanism for collecting said undesired material containing said desired material, and said extraction means collects said undesired material having said desired material while propelling across said surface for enabling collecting and separating to occur simultaneously;

a transport apparatus located between said front portion and said middle portion, said transport apparatus being adapted for receiving said undesired material containing said desired material from said extraction unit and to transport said undesired material containing said desired material to said middle portion;

said middle portion includes at least two cylinders which are mounted for rotation about a substantially horizontal axis, said at least two cylinders include a first cylinder having an inlet end and a last cylinder having an outlet end, to provide for said outlet end to be an opened end of said last cylinder;

each cylinder includes a first contact end and a second contact end and each second contact end of a preceding cylinder is in close proximity to a first contact end of a succeeding cylinder and at least one cylinder includes an encompassing wall with a screen that is perforated for progressively and selectively filtering said desired material from said undesired material from said inlet end to said outlet end and said outlet end extends into said back portion, and said outlet end extends into said back portion;

a receptacle for receiving said desired material is located in said back portion; and said second encompassing wall flares outwardly for providing said outlet end to be larger in size than said inlet end.

13. An apparatus as in claim 12 wherein said transport apparatus comprising a conveyor and said conveyor includes a first end and second end, said extraction unit is located in proximity to said first end and said second end is located in proximity of said middle portion, said conveyor is disposed at a slight angle to the true horizontal in an upward direction from said first end to said second end.

14. An apparatus as in claim 13 wherein said extraction unit includes a plurality of parallel, evenly spaced teeth that are normal to said undesirable material.

15. An apparatus as in claim 12 wherein said axis of rotation of said cylinder is disposed at a slight angle to the true horizontal in a downward direction from said opened inlet to said open outlet.

16. An apparatus as in claim 15 wherein said cylinders rotate in alternating direction.

17. An apparatus as in claim 12 wherein said back portion includes a platform that is located in the proximity of said opened outlet and is disposed at a slight angle to the true horizontal in a downward direction from said opened outlet, said platform includes a first side, a second side, a first end and a second end, said first end is located in the proximity of said opened outlet, a dividing plate extends perpendicularly and outwardly from said platform and divides said first side from said second side, and said receptacle is located on said second side for permitting said desired material to flow on said first side and fall into said receptacle and for larger portions of said undesired material to flow off said apparatus via said second side.

18. A method of separating desired material from an undesired material comprising the steps of:

(a) propelling a separating apparatus on a surface which contains said undesired material having said desired material, activating said separating for extracting and retrieving said undesired via an extracting device;

(b) transporting said undesired material containing said desired material via a transport apparatus to a separating area for separation of said desired material from said undesired material;

(c) passing said undesired material through a rotating cylinder, said rotating cylinder includes a plurality of sections, each section includes an encompassing side wall, and at least one encompassing side wall is perforated; and (d) transporting said desired material to a back portion for collecting and storing said desired material into a receptacle.

19. An apparatus as in claim 12 wherein said middle portion further includes and least one plate normal to said horizontal axis and is located between each section, and at least one opening is located between said cylinder and said plate.

* * * * *